(12) United States Patent
Lebel et al.

(10) Patent No.: US 7,510,552 B2
(45) Date of Patent: Mar. 31, 2009

(54) IMPLANTABLE MEDICATION DELIVERY DEVICE USING PRESSURE REGULATOR

(75) Inventors: Ronald J. Lebel, Sherman Oaks, CA (US); Stephen D. Das, The Woodlands, TX (US)

(73) Assignee: Infusion Systems, LLC, Valencia, CA (US)

( * ) Notice: Subject to any disclaimer, the term of this patent is extended or adjusted under 35 U.S.C. 154(b) by 0 days.

(21) Appl. No.: 11/203,532

(22) Filed: Aug. 12, 2005

(65) Prior Publication Data

US 2005/0273083 A1 Dec. 8, 2005

Related U.S. Application Data

(63) Continuation of application No. PCT/US2004/009534, filed on Mar. 24, 2004.

(60) Provisional application No. 60/458,151, filed on Mar. 27, 2003.

(51) Int. Cl.
*A61K 9/22* (2006.01)
*A61M 31/00* (2006.01)

(52) U.S. Cl. .................................. 604/891.1; 604/93.01

(58) Field of Classification Search ............. 604/891.1, 604/93.01, 890.1, 65–67, 288.01, 288.03, 604/288.04, 131, 141
See application file for complete search history.

(56) References Cited

U.S. PATENT DOCUMENTS

| | | | |
|---|---|---|---|
| 3,650,699 A | 3/1972 | Beer | |
| 3,731,681 A | 5/1973 | Blackshear et al. | |
| 4,074,694 A | 2/1978 | Lee | |
| 4,077,405 A | 3/1978 | Haerten et al. | |
| 4,152,098 A | 5/1979 | Moody et al. | |
| 4,193,397 A | 3/1980 | Tucker et al. | |
| 4,221,219 A | 9/1980 | Tucker | |
| 4,265,241 A | 5/1981 | Portner et al. | |
| 4,299,220 A | 11/1981 | Dorman | |
| 4,350,155 A | 9/1982 | Thompson | |
| 4,373,527 A | 2/1983 | Fischell | |
| 4,525,165 A | 6/1985 | Fischell | |
| 4,606,371 A | 8/1986 | Maekawa | |
| 4,714,462 A * | 12/1987 | DiDomenico | 604/67 |

(Continued)

FOREIGN PATENT DOCUMENTS

WO WO 99/38552 A1 8/1999

(Continued)

OTHER PUBLICATIONS

Supp. Search Report dated Aug. 14, 2008 in EPO App. Ser. No. 04 749 483.6.

*Primary Examiner*—Kevin C. Sirmons
*Assistant Examiner*—Catherine N Witczak
(74) *Attorney, Agent, or Firm*—Henricks, Slavin & Holmes LLP

(57) ABSTRACT

An implantable medication delivery apparatus including a flow path coupling a medication reservoir to a device outlet port where the flow path includes a regulator means for limiting the magnitude of pressure transferred downstream from the medication reservoir. The regulator means is configured to respond to the reservoir pressure exceeding a certain threshold for closing a valve located downstream from the reservoir. The valve closure functions to isolate the device outlet port from further reservoir pressure increases which otherwise could induce unintended medication flow from the device outlet port.

14 Claims, 6 Drawing Sheets

U.S. PATENT DOCUMENTS

| | | | |
|---|---|---|---|
| 4,718,893 A | 1/1988 | Dorman et al. | |
| 4,772,263 A | 9/1988 | Dorman et al. | |
| 4,832,054 A | 5/1989 | Bark | |
| 4,846,806 A | 7/1989 | Wigness et al. | |
| 4,968,301 A | 11/1990 | di Palma et al. | |
| 4,978,338 A | 12/1990 | Melsky et al. | |
| 5,061,242 A | 10/1991 | Sampson | |
| 5,067,943 A | 11/1991 | Burke | |
| 5,088,983 A | 2/1992 | Burke | |
| 5,158,547 A | 10/1992 | Doan et al. | |
| 5,342,298 A | 8/1994 | Michaels et al. | |
| 5,586,629 A | 12/1996 | Shoberg et al. | |
| 5,725,017 A | 3/1998 | Elsberry et al. | |
| 5,785,681 A * | 7/1998 | Indravudh | 604/65 |
| 5,820,589 A | 10/1998 | Torgerson et al. | |
| 5,957,890 A | 9/1999 | Mann et al. | |
| 6,048,328 A | 4/2000 | Haller et al. | |
| 6,152,885 A | 11/2000 | Taepke | |
| 6,152,898 A * | 11/2000 | Olsen | 604/93.01 |
| 6,203,523 B1 | 3/2001 | Haller et al. | |
| 6,228,050 B1 | 5/2001 | Olsen et al. | |
| 6,254,576 B1 | 7/2001 | Shekalim | |
| 6,290,652 B1 * | 9/2001 | Wellnhofer | 600/486 |
| 6,398,738 B1 | 6/2002 | Millar | |
| 6,488,652 B1 * | 12/2002 | Weijand et al. | 604/93.01 |
| 6,572,583 B1 | 6/2003 | Olsen et al. | |
| 2002/0088497 A1 | 7/2002 | Grey et al. | |
| 2003/0050623 A1 | 3/2003 | Lord et al. | |

FOREIGN PATENT DOCUMENTS

| | | | |
|---|---|---|---|
| WO | WO 00/74751 A1 | 12/2000 | |

* cited by examiner

IMPLANTABLE MEDICATION DELIVERY DEVICE USING PRESSURE REGULATOR

RELATED APPLICATIONS

This application is a continuation of PCT/US2004/009534 filed 24 Mar. 2004 and claims priority based on U.S. Application 60/458,151 filed 27 Mar. 2003.

FIELD OF THE INVENTION

This invention relates generally to implantable medication delivery systems, sometimes referred to as infusion pumps, and more particularly to a method and apparatus for enhancing safe operation by preventing unintended medication delivery attributable to reservoir overpressurization.

BACKGROUND OF THE INVENTION

Implantable medication delivery devices are widely discussed in the technical and patent literature. They typically include a housing containing a medication reservoir which can be filled transcutaneously by a hypodermic needle penetrating a fill port septum. The medication reservoir is generally coupled via an internal flow path to a device outlet port for delivering medication to the patient. A typical delivery device further includes some type of mechanism, e.g., a propellant chamber, for moving the medication from the reservoir through the internal flow path to the device outlet port for delivery to the patient.

The literature recognizes that overfilling the medication reservoir can result in unintended medication delivery from the device outlet port to the patient. Accordingly, various techniques have been proposed for avoiding problems associated with overfilling. For example, U.S. Pat. No. 5,158,547 describes an overfill protection mechanism comprising a valve associated with the fill port which automatically responds to a "reservoir full" condition to dose the fill port to prevent overfilling.

SUMMARY OF THE INVENTION

The present invention is directed to an implantable medication delivery apparatus including a flow path coupling a medication reservoir to a device outlet port where the flow path includes a regulator means for limiting the magnitude of pressure transferred downstream from the medication reservoir. Limiting the magnitude of pressure transfer prevents overpressurization of the reservoir from inducing an unintended delivery of medication from the device outlet port. More particularly, the regulator means is configured to respond to the reservoir pressure exceeding a certain threshold for closing a valve located downstream from the reservoir. The valve closure functions to isolate the device outlet port from further reservoir pressure increases which otherwise could induce unintended medication flow from the device outlet port.

In a preferred embodiment of the invention, the regulator means includes (1) a regulator medication chamber in the flow path between the reservoir outlet and the device outlet port; and (2) a regulator valve in the flow path between the reservoir outlet and the regulator chamber. In normal operation, the regulator valve is open and the pressure in the regulator chamber is substantially identical to the reservoir pressure. In the event of reservoir overpressurization attributable, for example, to abusive overfilling, the reservoir pressure and regulator chamber pressure will increase. When the regulator chamber pressure exceeds a certain threshold, the regulator valve closes to prevent further medication flow from the reservoir to the regulator chamber. Thus, any further rise in reservoir pressure will not increase regulator chamber pressure. After closure of the regulator valve, pressure within the regulator chamber will diminish as medication is periodically withdrawn therefrom for delivery to the device outlet port in accordance with the normal functioning (e.g., preprogrammed) of a medication delivery controller.

A regulator valve in accordance with the invention can be implemented in a variety of ways; e.g., it can include a pressure responsive element such as a bellows or a diaphragm mounted to move (e.g., expand or contract) in response to a sufficient pressure differential. The pressure responsive element is coupled to a valve element for movement between a seated (valve closed) state and an unseated (valve open) state. For example, the valve element can comprise a compliant disk mounted on an expansible bellows. During normal operation, when the reservoir and regulator chamber pressures are equal and less than a certain threshold pressure, the bellows unseats the disk, thus opening the medication flow path. However, when the regulator chamber pressure exceeds the certain threshold, the bellows contracts to seat the disk to thus close the flow path and prevent the elevated reservoir pressure from provoking unintended medication delivery through the flow path to the patient.

In accordance with the invention, the threshold level is based on a reference pressure which can be established in various ways. In one preferred embodiment, the reference pressure is derived from a substantially constant pressure available in a closed fixed volume chamber established at the time of manufacture. In a preferred embodiment, the closed chamber can comprise the compartment accommodating the electronics in the delivery device housing. Alternatively, the reference pressure can be derived from the outlet catheter, or from a site interior to the patient's body, e.g., the site of infusion, or exterior to the patient's body.

Various alternative regulator implementations can be employed in accordance with the invention to provide a pressure responsive element to move a valve element. The pressure responsive element can utilize, for example, a bellows or a diaphragm, which can either be attached to the valve element or bear against a biased valve element. Alternatively, the regulator can be implemented with a pressure responsive switch for controlling a solenoid to control position of a valve element.

Preferred embodiments of the invention utilize a pump located in the medication flow path between the regulator valve and the device outlet port. The pump is preferably powered by a battery carried by the implantable delivery device. A preferred regulator means in accordance with the invention derives its operating energy from the overpressurized reservoir and does not utilize battery power.

DETAILED DESCRIPTION

Figure 1:
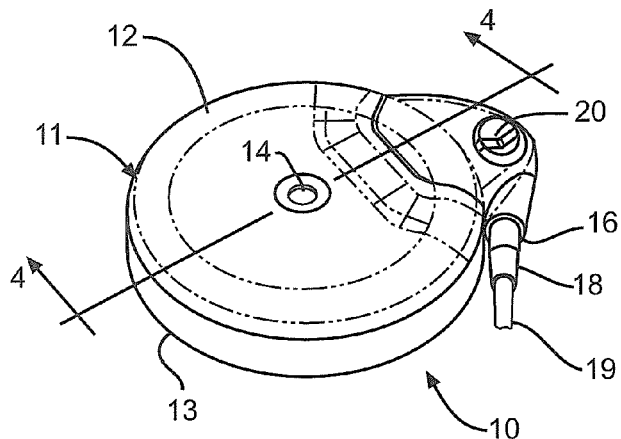
FIG. 1 is an isometric exterior view of a medication delivery device in accordance with the invention.

Attention is initially directed to FIG. 1 which illustrates the exterior of an exemplary medication delivery device 10 intended to be implanted in a patient's body for delivering medication to a body site, either on demand or in accordance with a programmed schedule. Devices having an appearance similar to that shown in FIG. 1 are well known in the art. The present invention is primarily directed to system improvements for enhancing safety by preventing overpressurization in an internal medication reservoir from unintentionally discharging medication into the patient's body.

Figure 3:
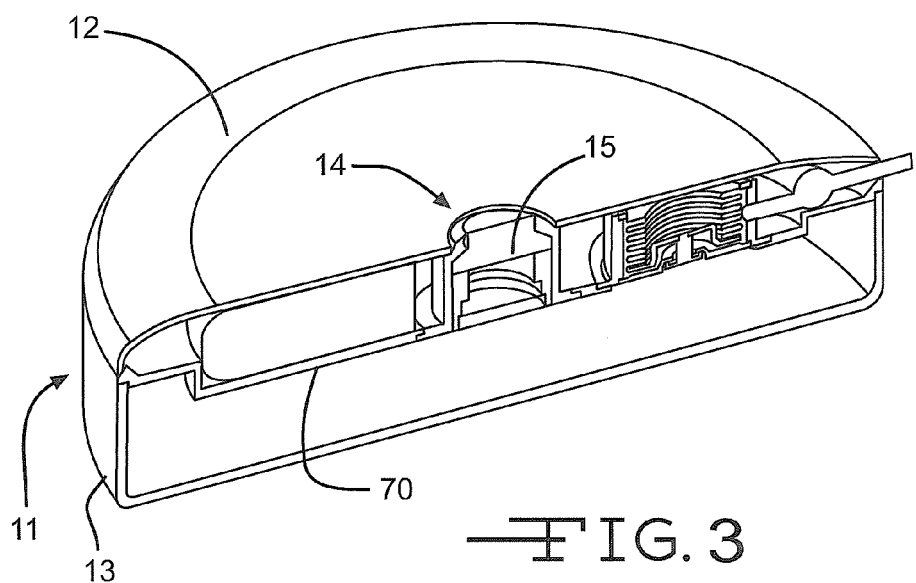
FIG. 3 is an isometric view of the device of FIG. 1 cut away to show its internal construction.

The device 10, as depicted in FIG. 1, is comprised of a housing 11 generally comprised of a cover 12 mounted on a case 13. The cover 12 defines a medication fill port 14 and a medication outlet port 16. A fitting 18 is shown coupled to the outlet port 16 for coupling to a catheter 19 whose distal end is intended to be implanted at an appropriate body site. FIG. 1 also illustrates a catheter access port 20 which permits bolus infusion through the fitting 18 to the implanted catheter (not shown). As will be discussed hereinafter, the housing 11 contains a medication reservoir which is selectively filled via fill port 14, typically using a hypodermic needle to penetrate a self healing septum 15 (FIG. 3) in the port 14. It is typical to design the medication reservoir so that it accommodates a certain maximum volume of fluid medication and withstands a certain related pressure for the device 10 to operate properly to deliver medication to the patient's body. If the medication volume in the reservoir and/or the reservoir pressure is exceeded, a potentially unsafe condition is created which could result in the unintended delivery of medication through the outlet port 16 to the patient. A system in accordance with the present invention is configured to detect such reservoir overpressurization and to quickly respond to prevent the unintended delivery of medication to the patient.

Figure 2:
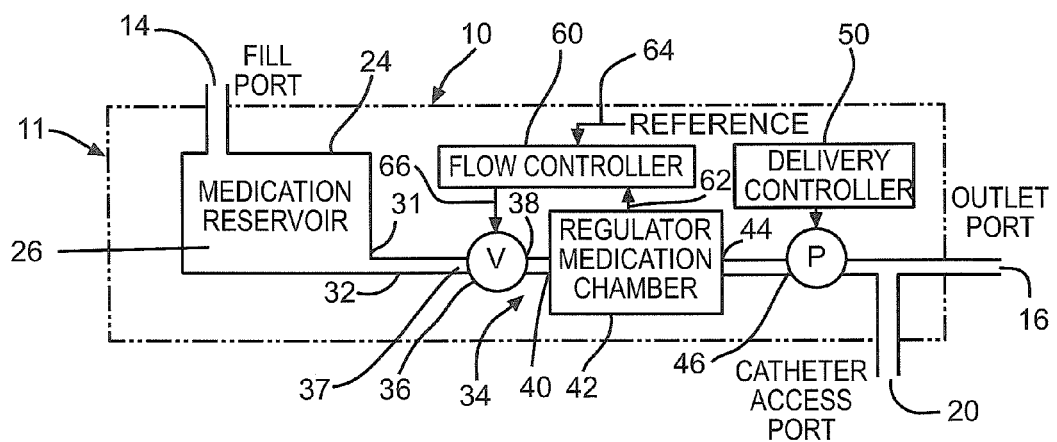
FIG. 2 is a functional block diagram of a medication delivery device in accordance with the invention.

FIG. 2 comprises a block diagram generally depicting a medication delivery system in accordance with the invention intended for mounting in the housing 11 of FIG. 1. For reference purposes, it is pointed out that FIG. 2 schematically depicts the housing 11 having a fill port 14, an outlet port 16, and a catheter access port 20, corresponding to the aforementioned elements pointed out in connection with the structural illustration of FIG. 1.

As shown in FIG. 2, the inlet port 14 communicates with the interior of a substantially closed medication reservoir 24 defining an interior volume 26. The reservoir volume 26 is coupled via reservoir outlet 31 to a flow path, generally designated as 32, which extends; to the device outlet port 16. In accordance with the present invention, the flow path 32 contains a pressure regulator means 34 operable to prevent excessively high reservoir pressure from being transferred downstream. The regulator means includes a normally open valve 36 connected in the flow path 32 downstream from the medication reservoir outlet 31. More particularly, the valve 36 has a valve inlet 37 coupled to the reservoir outlet 31 and a valve outlet 38 coupled to the inlet 40 of a regulator medication chamber 42. The chamber 42 defines an outlet 44 in the flow path 32 leading to outlet port 16. The chamber outlet 44 is preferably coupled to a battery operated pump 46 which is controlled by delivery controller 50 to periodically pull medication from the chamber 42 for transport downstream to the outlet port 16.

In normal operation of the system of FIG. 2, the medication reservoir 24 is filled via fill port 14 with a hypodermic needle. The valve 36 is normally open and accordingly the chamber 42 is continually replenished with medication from reservoir 24 and thus defines an internal pressure identical to the pressure within reservoir 24. In the event the pressure in reservoir 24 increases, attributable, for example, to an abusive overfilling, the pressure in the chamber 42 will also increase. In accordance with the invention, a flow controller 60 functions to compare the pressure in chamber 42 (represented by input 62) with a reference pressure (represented by input 64). When the pressure in chamber 42 exceeds a certain threshold pressure, the flow controller 60, via output 66, closes regulator valve 36. The closure of valve 36 acts to isolate the chamber 42 from further pressure increases in reservoir 24. Thus, overpressurization of the reservoir 24 will be isolated from and not bear on the medication in chamber 42, thus avoiding the unintended delivery of medication downstream from valve 36 through the outlet port 16.

In the normal operation of the medication delivery controller 50 and pump 46, increments of medication will be pumped from the chamber 42 and through the outlet port 16. Accordingly, over time, the pressure in chamber 42 will diminish. When the chamber pressure diminishes sufficiently, the flow controller 60 will open valve 36 to thereby again enable medication flow from the reservoir 24 to the chamber 42, thus initiating the process of relieving the overpressurization in the reservoir.

Whereas FIG. 2 depicts the functionality of a system in accordance with the invention, attention is now directed to FIGS. 3-6 which illustrates a preferred implementation. Note in FIGS. 3 and 4 that the housing 11 includes a partition 70 between the cover 12 and case 13. The partition 70 divides the housing interior volume into a lower compartment 72 and an upper compartment 74. The lower compartment 72 defines the aforementioned medication reservoir 24 configured to be filled via fill port 14 by a hypodermic needle inserted through aforementioned septum 15. A valve mechanism 78 (analogous to valve 36 of FIG. 2) is mounted in an opening 80 in the partition 70 for passing medication therethrough into a medication chamber 42 and then through pump 46 to a device outlet port 16. The valve mechanism 78 is normally open to permit medication flow from the reservoir 24 to the pump 46 and outlet port 16. However, as has been described in connection with FIG. 2, the valve mechanism 78 is configured to be closed by flow controller mechanism 82 when the reservoir pressure exceeds a certain threshold to prevent reservoir overpressurization from acting downstream to urge medication through pump 46 to outlet port 16.

Figure 5:
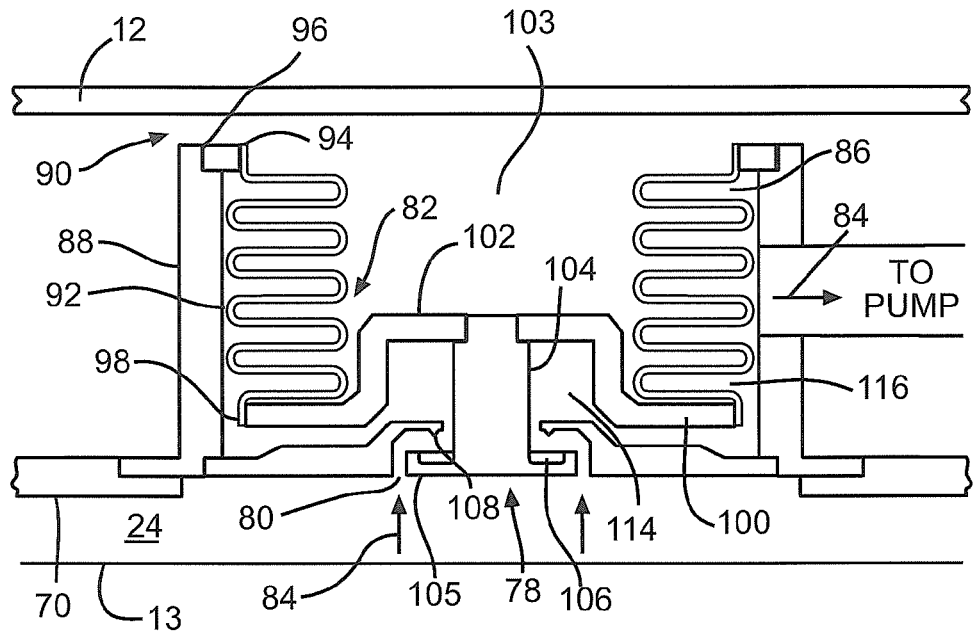
FIG. 5 is an enlarged sectional view of the regulator means of FIG. 1 showing the valve in the open state.
Figure 6:
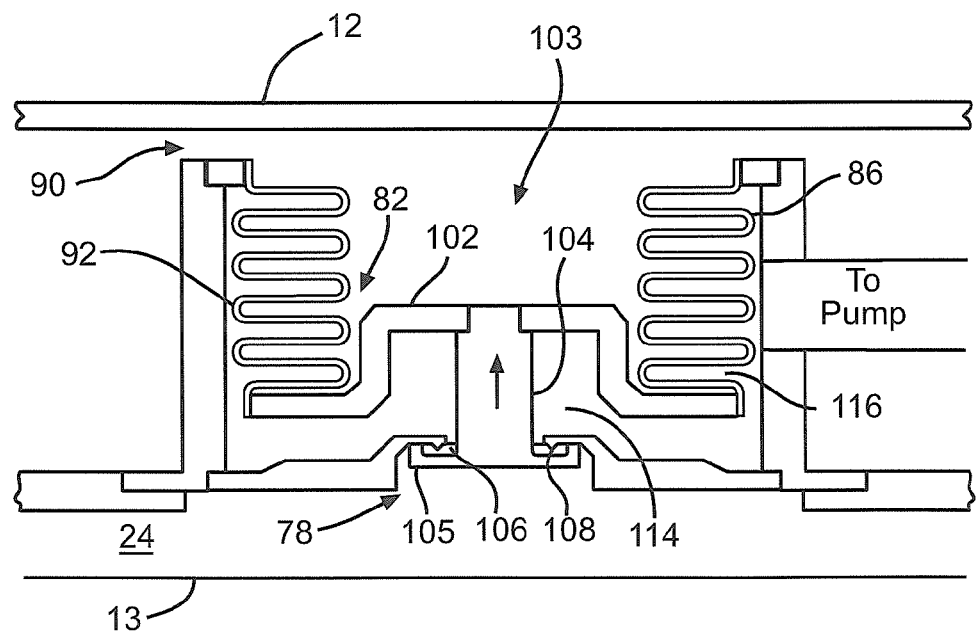
FIG. 6 is a sectional view similar to FIG. 5 showing the valve in the closed position.

FIGS. 5 and 6 illustrate a preferred implementation of the valve mechanism 78 and flow controller mechanism 82 in accordance with the present invention. FIG. 5 depicts the valve mechanism 78 in its normally open condition permitting medication flow (represented by flow arrows 84) from the reservoir 24 to the aforementioned pump 46. FIG. 6 illustrates the valve mechanism 78 in its closed state for isolating the reservoir from the flow path portion downstream from the valve mechanism 78. The flow controller 82 and valve mechanism 78 are mounted within a bore 86 defined by a cylindrical wall 88 projecting upwardly from the partition 70 above the aforementioned opening 80. Note that the wall 88 does not extend to the housing cover 12 but rather leaves a gap 90 therebetween. The flow controller mechanism 82 is comprised of a movable element, e.g., a bellows 92. The open upper peripheral edge 94 of the bellows is sealed at 96 to the top end of the wall 88. The lower peripheral edge 98 of the bellows is closed by a plate 100 having a central upwardly projecting offset portion 102 projecting into a bellows cavity 103.

The valve mechanism 78 is depicted as including a stem 104 which is suspended below the offset portion 102 of the wall 100. The lower end of the stem 104 defines a flange 105 which supports a valve element, e.g., a compliant disk 106. When the valve mechanism 78 is in its normally open position as illustrated in FIG. 5, the valve element 106 is spaced from, i.e., unseated, from valve nib 108. On the other hand, FIG. 6 illustrates the valve stem 104 pulled upwardly by the bellows 92 and plate portion 102 to seat the compliant valve element 106 against valve nib 108.

Figure 4:
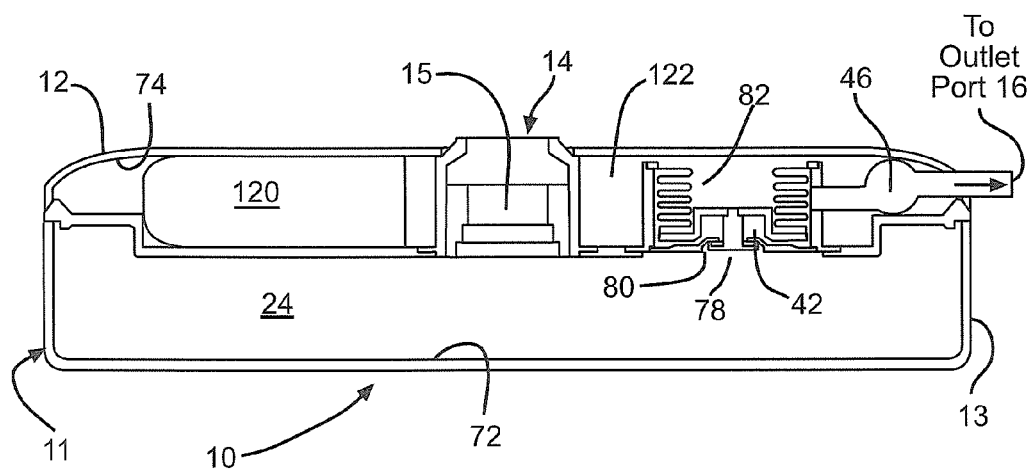
FIG. 4 is a vertical sectional view taken through the device of FIG. 1.

With reference to FIG. 4, it is pointed out that the upper compartment 74 is preferably used to house a battery 120 and electronic circuitry 122. The compartment 74 is sealed at the time of manufacture and contains a certain internal pressure which remains substantially constant over the useful life of the device 10, being relatively insensitive to moderate changes in ambient temperature and/or ambient pressure. The aforementioned gap 90 depicted in FIGS. 5 and 6 opens the cavity 103 to the upper compartment 74 so that the pressure within the cavity 103 above plate portion 102 also remains essentially constant. Thus, this upper compartment internal pressure is very suitable for use as a reference pressure to bear on the upper surface of plate portion 102. As long as the reference pressure is substantially equal to or greater than the pressure in reservoir 24, the plate portion 102 and stem 104 will be moved to the lowered position shown in FIG. 5 to unseat the valve element 106. With the valve element 106 normally open, medication can flow from the reservoir 24, past the valve element 106, past the valve seat 108, and through the region 114 and region 116 surrounding the bellows 92, to the pump 46. Regions 114 and 116 form a chamber analogous to medication chamber 42 of FIG. 2.

On the other hand, when a reservoir overpressurization condition occurs, i.e., the reservoir pressure exceeds a certain threshold, the pressure differential created across the plate portion 102 will be sufficient to pull valve element 106 upwardly to its seated position. More particularly, the upper surface of plate portion 102 sees the reference pressure available in the electronics compartment 74. The pressure condition in reservoir 24 acts on the lower surface of plate portion 102. The operational characteristics of the valve mechanism 78 are preferably selected so that the threshold pressure is slightly less than the reference pressure, i.e., valve closure preferably occurs prior to the reservoir pressure exceeding the reference pressure. When the valve element 106 is pulled upwardly against valve nib 108 (FIG. 6), it closes the flow path from the reservoir 24 to the regions 114, 116. This valve closure traps medication within the regions 114 and 116 which together function as the medication chamber 42 previously discussed in connection with FIG. 2.

The pump 46 located downstream from the regions 114 and 116 draws medication therefrom under the control of the aforementioned medication delivery controller 50. Thus, the patient is able to receive the intended medication delivery despite the overpressurization of reservoir 24. As medication is withdrawn from the regions 114 and 116 and delivered to the patient, the pressure differential across plate 100 will diminish. When it diminishes sufficiently, the reference pressure on the upper surface of plate 100 will be sufficient to drive the stem 104 downwardly to unseat the valve element 106 as shown in FIG. 5.

Figure 7:
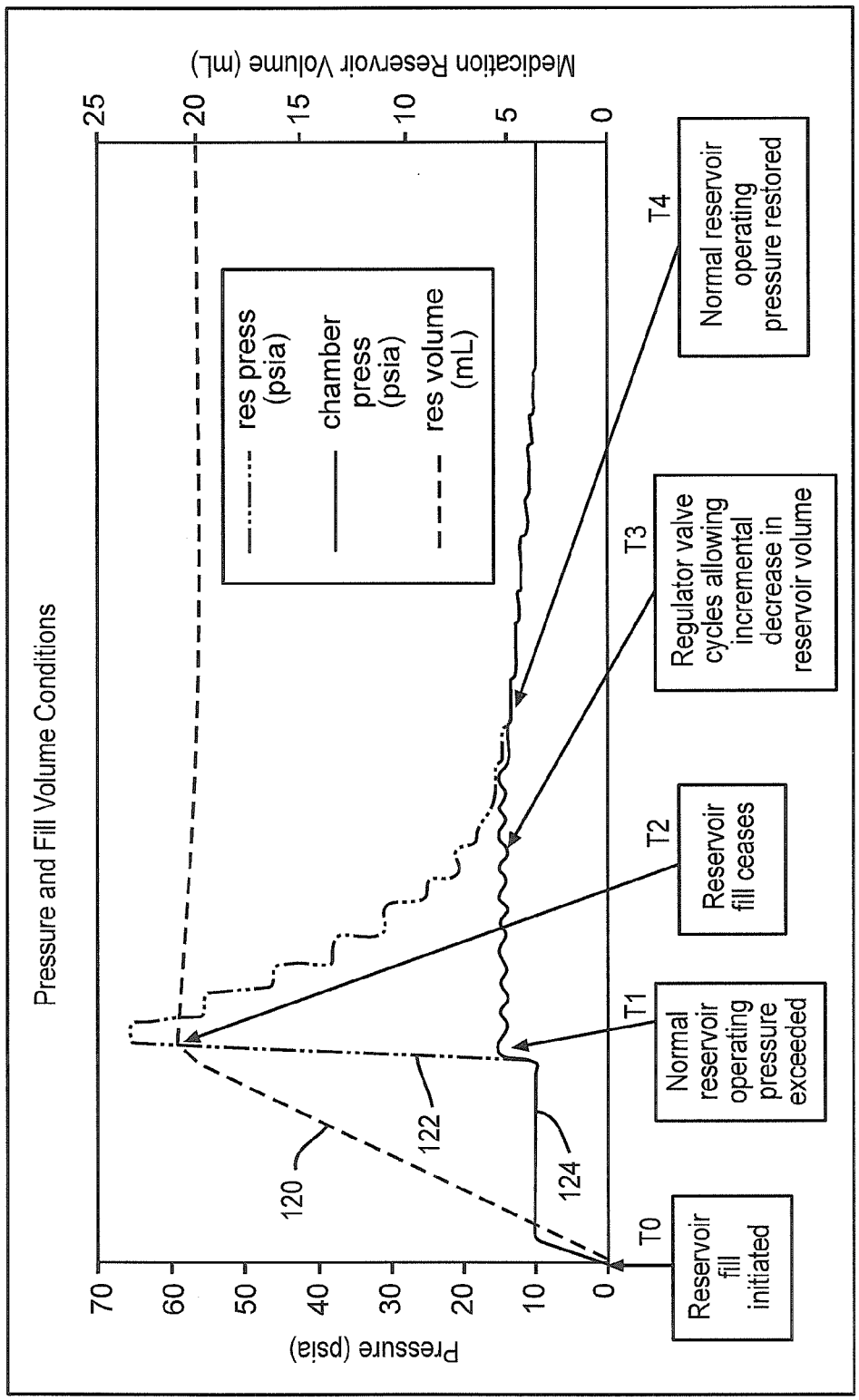
FIG. 7 graphically represents the operation of a device in accordance with the present invention.

FIG. 7 graphically illustrates an exemplary operation of a system in accordance with the invention. Note that at a certain point in time To the filling of the reservoir is initiated causing the reservoir volume curve 120 to ramp up. If filling continues beyond an intended level, then the reservoir pressure 122 will exceed its intended operating pressure at $T_1$. Note that the chamber pressure 124 tracks the reservoir pressure 122 from time $T_0$ to time $T_1$. At time $T_1$ the valve element 106 (FIGS. 5,6) closes to isolate the reservoir from the medication chamber regions 114, 116. Consequently, from time $T_2$ the chamber pressure will thereafter remain substantially constant except that it will decrease as medication is withdrawn therefrom during time $T_3$ by action of the pump 46. Accordingly, the valve 76 will cycle to periodically flow medication from the reservoir 24 into the medication chamber regions 114, 116. This action incrementally decreases the medication volume in the reservoir so that ultimately, at $T_4$, the normal reservoir operating pressure is restored.

Figure 8:
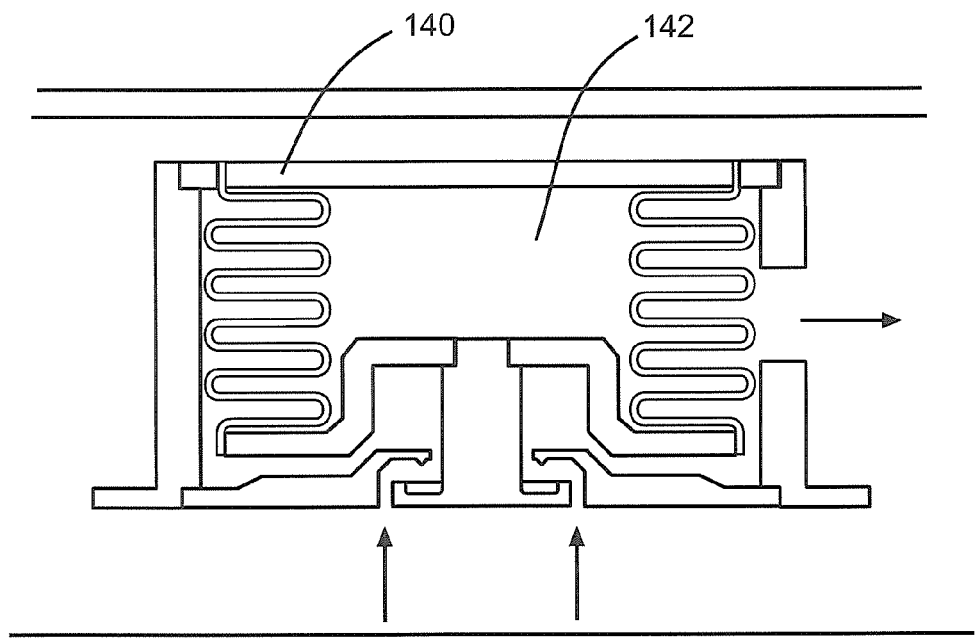
FIGS. 8 and 9 respectively show open and closed states for an alternative regulator means in accordance with the invention.
Figure 9:
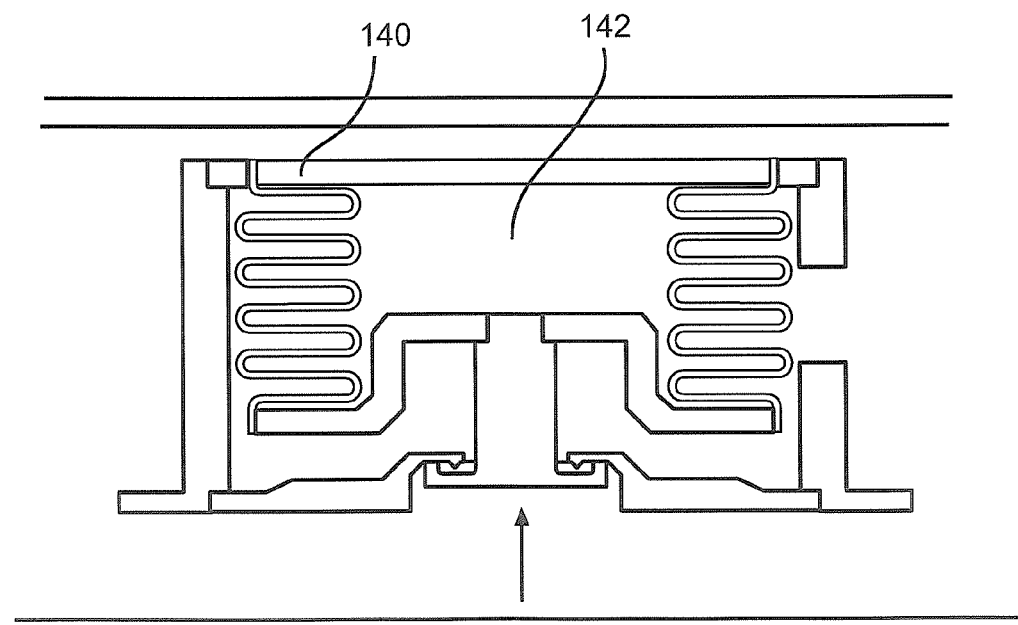

Whereas the embodiment thus far described with reference to FIGS. 5 and 6 utilizes the pressure within the upper electronics compartment as the reference pressure, FIGS. 8 and 9 illustrate a similar but alternative embodiment in which the upper end of the bellows is sealed by plate 140 to thus define a sealed internal cavity 142. The pressure in the cavity 142 is an engineered pressure established at time of manufacture for reference purposes. Alternatively, other embodiments can derive the reference pressure from other sites such as at the catheter outlet, or at another body site.

Figure 10:
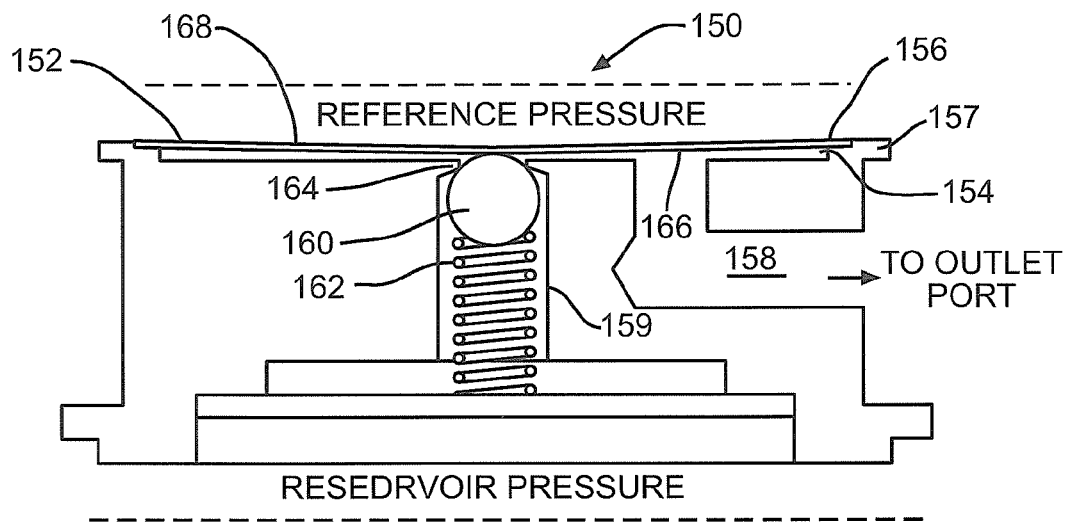
FIG. 10 is a schematic view of a further alternative regulator means.

Attention is now directed to FIG. 10 which depicts a further implementation 150 of a regulator means in accordance with the present invention. The regulator means 150 employs a diaphragm 152 as the pressure responsive element. The diaphragm is mounted over a shallow cavity 154 by sealing the peripheral edge 156 of the diaphragm to a flange 157 surrounding the cavity 154. The cavity 154 functions as the regulator medication chamber (42 in FIG. 2) and is coupled via passage 158 to the device outlet port, preferably via a battery operated pump as shown in FIG. 2. The flow path from the reservoir (not shown in FIG. 10) includes a portion 159 opening into cavity 154 beneath the diaphragm 152. The path portion 159 accommodates a ball valve element 160 and a spring 162 which act to urge the element 160 to a seated position against valve seat 164.

It should be noted that the diaphragm lower surface 166 is exposed to reservoir pressure via path portion 159 and the diaphragm upper surface 168 is exposed to a reference pressure; e.g., the pressure in the device electronics chamber as previously discussed.

In normal operation when the reservoir pressure is less than the reference pressure, the diaphragm 152 is flexed downwardly to bear against valve element 160 to compress spring 162 to unseat the element 160 and open the flow path from the reservoir to the cavity 154. However, when the reservoir pressure increases above a certain threshold, the diaphragm 152 flexes upwardly, to enable the spring 162 to seat the valve element 160 against valve seat 164. This action isolates the flow path portions downstream from valve element 160 from further reservoir pressure increases.

Figure 11:
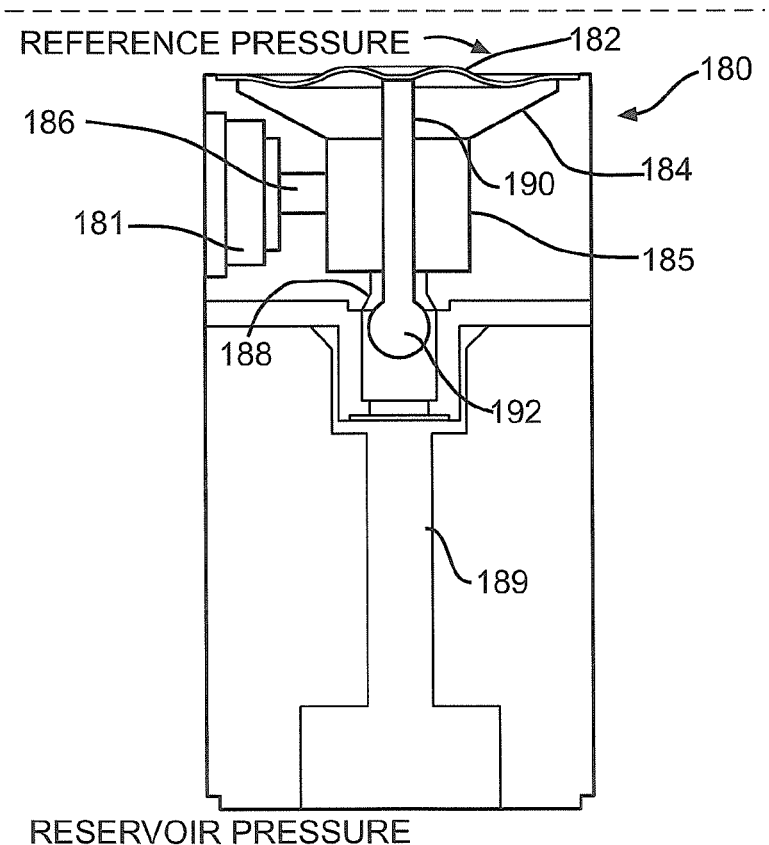
FIG. 11 is a schematic view of a still further alternative regulator means.

Attention is now directed to FIG. 11 which depicts a still further implementation 180 showing a regulator means integrated with a pump 181. Regulator means 180 employs a diaphragm 182 as the pressure responsive element. The diaphragm 182 is mounted over a shallow cavity 184 which forms part of the regulator medication chamber 185. The flow path from the reservoir (not shown in FIG. 11) includes a path portion 186, containing a valve seat 188, leading to the medication chamber 185. A conduit 189 extends from chamber 185 toward the device outlet port (not shown in FIG. 11).

The diaphragm 182 has a stem 190 depending therefrom which terminates in a ball valve element 192. The diaphragm 182 is normally flexed downwardly as illustrated to unseat the ball element 192 from valve seat 188. However, as with the previously discussed embodiments, when the reservoir pressure applied to the underside of diaphragm 182 (via path portion 186 and medication chamber 185) exceeds the reference pressure applied to the upper surface of diaphragm 182, the diaphragm flexes upwardly to pull the ball element 192 and seat it against valve seat 188. This action then isolates the medication chamber 185 from further pressure increases in the reservoir.

From the foregoing, it should now be appreciated that an implantable medication delivery device apparatus and method have been described herein incorporating a flow path between a reservoir and an outlet port which includes a regulator means operable to contain excessive reservoir pressure excursions. The regulator means functions to prevent excessive reservoir pressure from acting downstream to force medication through the outlet port. Although only a limited number of embodiments have been specifically described herein, it should be recognized that the invention can be implemented in a variety of alternative manners which fall within the intended scope of the appended claims. For example only, in addition to using a bellows and/or diaphragm for pressure sensing and valve element control, the regulator means can be implemented using a pressure responsive switch to control a solenoid and valve element.

The invention claimed is:

1. An implantable medication delivery device, comprising;
   an implantable housing having a medication reservoir compartment, a fill port connected to the medication reservoir compartment, a sealed electronics compartment configured to maintain a substantially constant internal pressure therein, and an outlet port operably connected to the medication reservoir compartment;
   at least one electronic device located within the sealed electronics compartment; and
   a normally opened passive valve located within the implantable housing and including a valve element, movable between an open position that allows medication flow and a closed position that prevents medication flow, and a pressure responsive structure, operably connected to the valve element, having a first surface exposed to the substantially constant internal pressure of the sealed electronics compartment and a second surface exposed to medication flow within the implantable housing;
   wherein the valve element and pressure responsive structure are respectively configured and positioned such that the valve element will move to the closed position when the pressure of the medication flow reaches a threshold pressure.

2. An implantable medication delivery device as claimed in claim 1, wherein the threshold pressure is slightly less than the substantially constant internal pressure of the sealed electronics compartment.

3. An implantable medication delivery device as claimed in claim 1, wherein the pressure responsive structure includes a bellows, defining a first end, a second end and an interior, and a plate that closes the first end of the bellows.

4. An implantable medication delivery device as claimed in claim 1, wherein the normally opened passive valve is located between the medication reservoir compartment and the outlet port.

5. An implantable medication delivery device as claimed in claim 1, further comprising:
   a pump located between the normally opened passive valve and the outlet port.

6. An implantable medication delivery device as claimed in claim 1, wherein the direction of medication flow through the passive valve is from the valve element to the pressure sensitive structure.

7. An implantable medication delivery device as claimed in claim 1, wherein the at least one electronic device comprises electronic circuitry.

8. An implantable medication delivery device as claimed in claim 1, further comprising:
   a battery located within the sealed electronics compartment.

9. An implantable medication delivery device, comprising:
   an implantable housing having a medication reservoir compartment, a fill port connected to the medication reservoir compartment, a sealed electronics compartment configured to maintain a substantially constant internal pressure therein, and an outlet port operably connected to the medication reservoir compartment; and
   a normally opened passive valve located within the implantable housing and including
      a tubular wall, defining a first end and a second end, and a valve seat adjacent to the first end of the tubular wall,
      a valve element movable between an open position that allows medication flow and a closed position that prevents medication flow, and
      a pressure responsive bellows that is located within the tubular wall, operably connected to the valve element, defines a first end, a second end secured to the second end of the tubular wall, and an interior exposed to the substantially constant internal pressure of the sealed electronics compartment, and has a plate exposed to medication flow within the implantable housing that closes the first end of the bellows;
   wherein the valve element and bellows are respectively configured and positioned such that the valve element will move to the closed position when the pressure of the medication flow reaches a threshold pressure.

10. An implantable medication delivery device as claimed in claim 9, wherein the tubular wall comprises a substantially cylindrical wall.

11. An implantable medication delivery device as claimed in claim 9, wherein
   the medication reservoir compartment and the sealed electronics compartment are separated by a partition; and
   the first end of the tubular wall is secured to the partition.

12. An implantable medication delivery device as claimed in claim 11, wherein
   the implantable housing includes a cover;
   the sealed electronics compartment is defined by the cover and the partition; and
   the second end of the tubular wall is separated from the cover by a small gap.

13. An implantable medication delivery device as claimed in claim 9, wherein
   the valve element comprises a compliant disk that is configured to mate with the valve seat; and
   the compliant disk is secured to the plate by a valve stem.

14. An implantable medication delivery device as claimed in claim 9, wherein the tubular wall includes an aperture between the first and second ends.

* * * * *